(12) United States Patent
Gerstenmeier

(10) Patent No.: US 9,278,232 B2
(45) Date of Patent: Mar. 8, 2016

(54) DEVICE FOR IRRADIATING ACTINIC RADIATION OF DIFFERENT WAVELENGTHS

(75) Inventor: Juergen Gerstenmeier, Windhagen (DE)

(73) Assignee: JK-HOLDING GMBH, Winghagen (DE)

( * ) Notice: Subject to any disclaimer, the term of this patent is extended or adjusted under 35 U.S.C. 154(b) by 0 days.

(21) Appl. No.: 13/421,672

(22) Filed: Mar. 15, 2012

(65) Prior Publication Data

US 2012/0238939 A1 Sep. 20, 2012

(30) Foreign Application Priority Data

Mar. 17, 2011 (EP) ..................................... 11002217

(51) Int. Cl.
*A61N 5/06* (2006.01)
(52) U.S. Cl.
CPC .......... *A61N 5/0616* (2013.01); *A61N 2005/064* (2013.01); *A61N 2005/0637* (2013.01); *A61N 2005/0659* (2013.01); *A61N 2005/0662* (2013.01)
(58) Field of Classification Search
CPC .. A61N 5/0616; A61N 2005/0665–2005/0667
USPC ...................................................... 607/88–91
See application file for complete search history.

(56) References Cited

U.S. PATENT DOCUMENTS

| | | | |
|---|---|---|---|
| 4,909,254 A | 3/1990 | Wilkinson | |
| 6,443,978 B1 | 9/2002 | Zharov | |
| 6,717,164 B2 * | 4/2004 | Ullrich et al. | 250/504 R |
| 8,274,064 B2 | 9/2012 | Manstein | |
| 2004/0008523 A1 | 1/2004 | Butler | |
| 2004/0193234 A1 | 9/2004 | Butler | |
| 2005/0085877 A1 | 4/2005 | Kratz | |
| 2005/0149150 A1 | 7/2005 | McDaniel | |
| 2006/0111761 A1 | 5/2006 | Butler | |
| 2007/0007470 A1 | 1/2007 | Kratz | |
| 2007/0030662 A1 | 2/2007 | Hsu | |
| 2007/0073365 A1 | 3/2007 | Butler | |
| 2007/0097691 A1 * | 5/2007 | Wu | 362/293 |
| 2007/0139930 A1 | 6/2007 | Spivak | |
| 2007/0208395 A1 | 9/2007 | Leclerc et al. | |
| 2009/0118799 A1 | 5/2009 | Nanninga | |
| 2009/0146086 A1 | 6/2009 | Manstein | |
| 2009/0222070 A1 | 9/2009 | Daffer | |
| 2009/0240310 A1 * | 9/2009 | Kennedy | 607/89 |
| 2009/0270848 A1 | 10/2009 | Weckwerth et al. | |

(Continued)

FOREIGN PATENT DOCUMENTS

| | | | | |
|---|---|---|---|---|
| DE | 3927695 A1 * | 2/1991 | ............... | A61N 5/06 |
| DE | 102005030388 A1 | 1/2007 | | |

(Continued)

*Primary Examiner* — Lynsey Crandall
*Assistant Examiner* — Nathan J Jenness
(74) *Attorney, Agent, or Firm* — Abel Law Group LLP

(57) ABSTRACT

Described is a device for irradiating a body with actinic radiation. The device comprises one or more elements allowing the person to stand, sit or lie in a position allowing said actinic radiation to impinge on at least a part of the body; one or more elements allowing control of the intensity, irradiance, dose, and/or time of irradiation of said actinic radiation; and one or more elements comprising at least one source of radiation that emits radiation of at least two different wavelengths, at least one of the wavelengths being in the visible range.

10 Claims, 6 Drawing Sheets

(56) References Cited

U.S. PATENT DOCUMENTS

| | | |
|---|---|---|
| 2010/0137950 A1 | 6/2010 | McDaniel |
| 2012/0078328 A1* | 3/2012 | Vancraeyenest et al. ........ 607/88 |
| 2012/0101557 A1 | 4/2012 | Wagenaar Cacciola et al. |
| 2012/0123507 A1 | 5/2012 | Whitehurst |

FOREIGN PATENT DOCUMENTS

| | | | |
|---|---|---|---|
| DE | 202009004449 U1 | 7/2009 | |
| DE | 202010005063 U1 | 8/2010 | |
| EP | 1508301 A2 | 2/2005 | |
| EP | 2055349 A2 | 5/2009 | |
| RU | 2144396 C1 | 1/2000 | |
| RU | 2195981 C2 | 1/2003 | |
| RU | 72411 U1 | 4/2008 | |
| WO | WO 90/00420 A1 * | 1/1990 | ............... A61N 5/06 |
| WO | 2005011606 A2 | 2/2005 | |
| WO | 2007106856 A2 | 9/2007 | |
| WO | 2008027438 A2 | 3/2008 | |
| WO | 2008110963 A1 | 9/2008 | |
| WO | 2009076306 A2 | 6/2009 | |
| WO | 2010070277 A1 | 6/2010 | |
| WO | 2010150165 A1 | 12/2010 | |

* cited by examiner

DEVICE FOR IRRADIATING ACTINIC RADIATION OF DIFFERENT WAVELENGTHS

CROSS-REFERENCE TO RELATED APPLICATIONS

The present application claims priority under 35 U.S.C. §119 of European Patent Application No. 11 002 217.5, filed Mar. 17, 2011, the entire disclosure of which is expressly incorporated by reference herein.

BACKGROUND OF THE INVENTION

1. Field of the Invention

The present invention relates to a device which is capable of emitting, and thereby irradiating onto a subject, actinic radiation of different wavelengths. In particular, the invention relates to a device capable of emitting, and thereby irradiating onto a subject, actinic radiation of two different specified wavelengths having at least one physiological effect or even more than one physiological effect. In case of two, three or more physiological effects, these physiological effects may have a synergistic effect for the subject irradiated.

2. Discussion of Background Information

Devices for irradiating actinic radiation onto a subject, for example onto a human user intending to become exposed to such actinic radiation, are known. Such known devices, particularly those suitable to irradiate actinic radiation onto the whole body of a user, belong to groups which may either be divided according to the position the user has to take when being exposed to the radiation, or may be divided according to the type (or, largely, the wavelength or wavelength range) of the radiation which is irradiated onto the subject's, or user's, body.

Thus, what concerns the user's position when being irradiated, there may be distinguished devices for irradiating the subject's, or user's, body while the body is in a horizontal position, which devices, for obvious reasons, are often also called "beds", or devices for irradiating the subject's, or user's, body while the body is in a vertical position, which position may be a sitting or standing position. Both groups of irradiation devices are included in the present invention.

What concerns the type of radiation irradiated onto the subject's, or user's, body, the known devices of the prior art are largely divided according to the wavelength, or wavelength range, of the actinic radiation irradiated onto the user's body.

Well known are devices for irradiating UV radiation, mainly UV radiation of the UV-A (320 to 400 nm) and UV-B (280 to 320 nm) range, onto a user's body. Such tanning devices, either in the form of tanning beds or in the form of vertically arranged tanning apparatus, are known, for example, from DE 10 2005 030 388 and EP 2 055 349, the entire disclosures of which are incorporated by reference herein, and are also known from other patent applications.

Also known are lamps, and irradiation devices comprising such lamps, for stimulating the vitamin D production in the body of a user of such a device, by an irradiation of the user's body with light having a wavelength in the range of from 250 nm to 320 nm, with a peak at a wavelength of about 296 nm. An example documents relating to such lamps is WO 2008/027438, the entire disclosure of which is incorporated by reference herein.

Recently, there were also disclosed devices for activating the collagen production in the skin of the user exposed to actinic radiation having a wavelength in the range of 610 to 650 nm, with a peak wavelength being at 620 nm. Examples of documents disclosing actinic radiation for an activation of the collagen production in the skin are DE 20 2009 004 449 U (to KBL Solarien AG) and D 20 2010 005 063 U (to Hapro International B.V.), the entire disclosures of which are incorporated by reference herein.

In the above-mentioned documents to KBL and Hapro the actinic radiation emitted to the user's body and having the effect of activating the collagen production in the user's skin is accompanied by emitted UV radiation, in the former case by UV-A and UV-B radiation having a tanning activity, while in the latter case, the UV-A radiation portion is at a minor dose and the UV-B radiation portion is at most equivalent to 0.5 MED (minimum erythemal dose) so that a tanning effect is not achieved.

As described above, actinic radiation has certain physiological effects onto the body of a user, particularly a human subject. As is well known for irradiating UV radiation (either natural UV radiation impinging onto the ground of the earth as a result of the emission of the natural sun radiation or artificially generated UV radiation, mainly in the UV-A and UV-B range of wavelengths) onto the human body, a certain UV radiation dose may have beneficial physiological effects to the user's skin, but an overdose (i.e. a dose above a determined value (i.e. the MED or minimum erythemal dose value)) may harm the body. In acknowledging the risks of UV radiation doses exceeding the MED, the EU recently introduced a legislation restricting the emitted UV-B radiance of artificially generated actinic radiation in the UV wavelength range to a value of a so-called "erythemally effective" radiance $E_{er}$ of 0.3 W/m².

However, less severe restrictions apply to non-UV radiation. This results, at best, into observing the legally binding limits for UV radiation by manufacturers, operators and/or users, but does not restrict devices emitting actinic radiation in other wavelength ranges achieving physiological effects, when such radiation impinges onto the user's body/skin in a dose or for a time exceeding physiologically acceptable dose or radiance values. This is, particularly, a problem in a situation where a certain physiological effect can be obtained only by a certain minimum dose of actinic radiation due to the fact that the radiation has to reach a certain depth of the skin in order to become effective, and such effective depth is not achieved with low doses or weaker radiances of the irradiated radiation.

Hence, it would be advantageous to be able to provide a device for irradiating a body of a subject or a person or a user with actinic radiation of at least two different physiologically effective wavelengths, of which at least one is in the range of visible wavelengths.

In addition, it would be advantageous to be able to provide a device for irradiating a body of a subject or a person or a user with actinic radiation of at least two different physiologically effective wavelengths, which device is safe and does not deliver actinic radiation in a dose and range detrimental to the user's body.

In addition, it would be advantageous to be able to improve, and maintain already on the manufacturer's level without allowing the device to grant users the freedom to circumvent the measures required, the safety of devices emitting actinic radiation to the body of a user in wavelength ranges from the UV wavelength range to the range of longer wavelengths.

Surprisingly, some or all of the above advantages may be achieved by the device of the present invention, particularly due to the fact that the device of the invention comprises elements comprising at least one source of radiation, said source(s) of radiation emitting radiation of at least two different wavelengths having at least one physiological effect on the body of said subject/person/user of the device, of which radiation wavelength(s) at least one is in the visible range, said radiation of the at least two different wavelengths being directed to at least a part of the body of said subject/person/user.

SUMMARY OF THE INVENTION

The present invention provides a device for irradiating a body of a subject/person/user with actinic radiation of at least two different wavelengths. The device comprises (i) one or more elements for allowing the subject/person/user to stand on a stand, sit on a seat or lie on a bed in a position allowing said actinic radiation to impinge on at least a part of the body of said subject/person/user while on the stand, seat or bed; one or more elements allowing a control of the intensity, irradiance, dose, and/or time of irradiation of said actinic radiation to be irradiated and/or irradiated onto the body of said subject/person/user; and one or more elements comprising one or more sources of radiation, said source(s) of radiation emitting radiation of at least two different wavelengths having at least one physiological effect on the body of said subject/person/user, of which radiation wavelengths at least one is in the visible range, said radiation of the at least two different wavelengths being directed to at least a part of the body of said subject/person/user.

In one aspect of the device of the present invention, the one or elements for allowing a control of the intensity, dose, and/or time of irradiation of said actinic radiation may comprise one or more elements for determining the skin status, preferably the skin tan status, and/or the skin type of the person to be irradiated with said actinic radiation. For example, the result of the determination, by said control elements, of the skin status and/or the skin type of the person to be irradiated and/or irradiated may allow a direct control of the intensity, irradiance, dose, and/or time of irradiation of said actinic radiation.

In another aspect of the device, the radiation of at least one wavelength may be in the range of visible wavelengths, and the radiation of at least one different wavelength may be in the range of non-visible wavelengths. For example, the radiation of the at least one wavelength in the range of non-visible wavelengths may be radiation of a wavelength selected from about 810 to about 850 nm, preferably of a wavelength selected from about 820 to about 840 nm, and/or the radiation of at the least one wavelength in the range of visible wavelengths may be radiation of a wavelength selected from about 570 to about 780 nm, preferably of a wavelength selected from the ranges of from about 570 nm to about 610 nm, from about 610 nm to about 650 nm, from about 650 nm to about 690 nm and from about 740 to about 780 nm and combinations thereof.

In a still further aspect of the device of the present invention, at least one radiation of the at least one wavelength emitted by the at least one source of radiation may be emitted in a narrow wavelength band and may preferably be emitted by at least one type of low pressure lamp and more preferably may be emitted by at least one type of Light Emitting Diode (LED) and/or by at least one type of low-pressure tube lamp containing at least one light-emitting phosphor.

In yet another aspect of the device, at least one radiation of the at least one wavelength emitted by the at least one source of radiation may be emitted in a broad wavelength band and may preferably be emitted by at least one type of high pressure lamp and may more preferably be emitted by at least one type of high-pressure discharge lamp. For example, the device may further comprise a filter allowing the passage of radiation of at least one well-defined wavelength band, preferably allowing the passage of radiation of a wavelength band in the range of from 570 to 780 nm, more preferably in the range selected from about 570 nm to about 610 nm, from about 610 nm to about 650 nm, from about 650 nm to about 690 nm and from about 740 to about 780 nm and combinations thereof, and/or preferably allowing the passage of radiation of a wavelength band in the range of from about 810 to about 850 nm, more preferably in the range of from about 820 to about 840 nm.

In particular, a filter may be used that allows the passage of radiation within a range of wavelengths v, wherein v is defined by v≥about 570 nm; preferably v is defined by about 570 nm≤v≤about 950 nm.

More preferably, a filter having the following filter performance characteristics may used:
$T_{avg}$>85%@about 650 to about 850 nm;
$T_1$=50%@about 610±10 nm;
$T_{avg}$>1%@<about 570 nm;
Most preferably, a filter having the following filter performance characteristics may be used:
$T_{avg}$<15%@about 1100 to about 2500 nm;
$T_2$=50%@about 900±20 nm;
$T_{avg}$>85%@about 650 to about 850 nm;
$T_1$=50%@about 610±10 nm;
$T_{avg}$<1%@<about 570 nm.

For example, in one aspect a filter may be used having at least one coating allowing the passage actinic radiation of long wavelengths, preferably a filter may be used having at least one coating selected from a coating comprising $SiO_2$ and a coating comprising $TiO_2$ and a coating comprising combinations thereof, or a filter may be used having at least one coating allowing the passage of actinic radiation of short wavelengths and having at least one coating allowing the passage of actinic radiation of long wavelengths, preferably a filter having at least one coating selected from a coating comprising ITO (indium tin oxide), a coating comprising $SiO_2$ and a coating comprising $Ta_2O_5$ and a coating comprising combinations thereof, and at least one coating selected from a coating comprising $SiO_2$ and a coating comprising $TiO_2$ and a coating comprising combinations thereof.

The present invention also provides to the device set forth above (including the various aspects thereof) for use in medicine and/or for use in the cosmetic field.

Preferred medical uses of the device of the present invention include the use for the treatment of ageing skin, of sunburn and/or erythema resulting from excessive exposition of the skin to UV radiation, of acne, of skin irritation, inflammations of the skin and of psoriasis.

Preferred cosmetic uses of the device of the present invention include the use for the treatment of ageing skin by causing the skin to effect collagenogenesis and/or hyaluronic acid genesis and/or elastinogenesis upon irradiation by visible light in the wavelength range of 570 to 780 nm, more preferably in the ranges of from 570 nm to 610 nm, from 610 nm to 650 nm, from 650 nm to 690 nm and/or from 740 to 780 nm and/or upon irradiation by non-visible light in the wavelength range of from 810 to 850 nm, without any additional application of any cosmetic composition or in combination with usual cosmetic preparations, preferably applied to the skin for a treatment of ageing skin.

BRIEF DESCRIPTION OF THE DRAWINGS

The invention is described below by a description of preferred embodiments thereof, while referring to the Figures, wherein.

DETAILED DESCRIPTION OF THE PRESENT INVENTION

Figure 1:
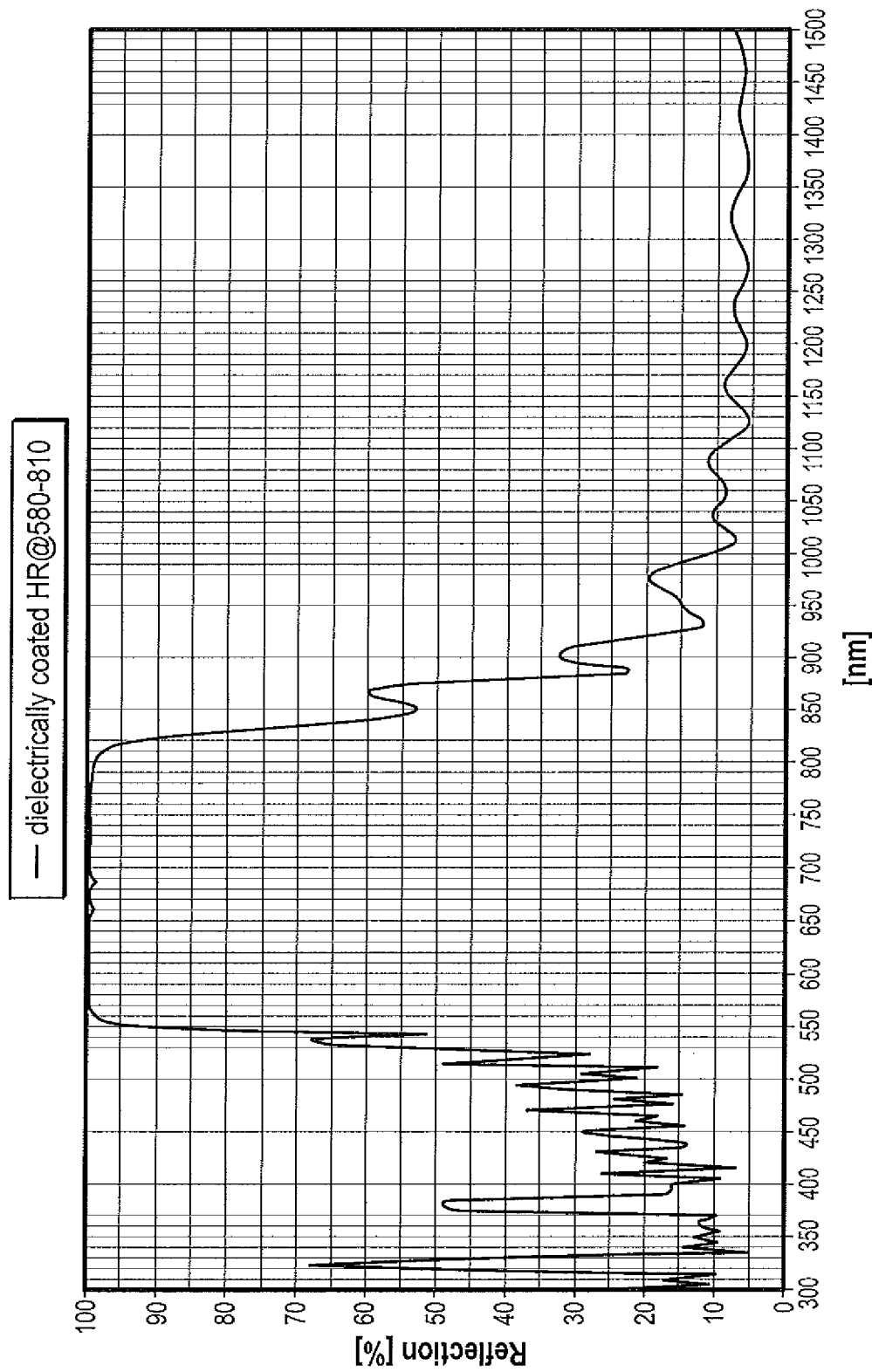
FIG. 1 shows an actinic light emission spectrum of a reflector of a preferred actinic light-emitting high pressure lamp/reflector/filter combination in accordance with a preferred embodiment of the invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description in combination with the drawings making apparent to those skilled in the art how the several forms of the present invention may be embodied in practice.

The terms "subject", "person" and "user" are used in the present specification and claims synonymously and mean the person which uses the device of the present invention for being irradiated by the actinic radiation; of course, the person is subject of such irradiation by the device of the invention.

The terms "comprise", "comprises" or "comprising" as used in the present specification and appended claims have the meaning that the device of the invention may comprise (i) one element or may comprise (ii) two or more elements as mentioned in, for example, claim 1, or that (iii) further components, elements etc. (more specifically defined below) may also be comprised by the device.

The terms "comprise", "comprises" or "comprising" as used in the present specification and appended claims may, however, also include cases where the device of the invention essentially consists of (i) at least one element or essentially consists of (ii) two or more elements mentioned, for example, in claim 1, optionally together with any necessary component or element a skilled person may include into such a device in order to achieve the object of the invention, or may even include cases where the device of the invention exclusively consists of (i) at least elements or exclusively consists of (ii) two or more elements, optionally, but not necessarily, together with any necessary component, element etc. a skilled person may include into such a composition in order to achieve the object of the invention. Particularly in the latter case where the terms "comprise", "comprises" or "comprising" as used in the present specification and claims may have the meaning of an "exclusively consisting of", dependent claims of the present application may claim, and corresponding parts of the specification may describe, further preferred embodiments, which are characterized by additional specified features which, in combination with the features of the independent claim and corresponding parts of the description, are summarized to belong to the invention as described in its broadest scope claimed.

In other words: The terms "comprise" or "comprises" or "comprising" may have, in the present specification and claims, the meaning of describing a non-exhaustive enumeration of elements or, alternatively, may have, in the present specification and claims, the meaning of describing an exhaustive enumeration of elements, in the latter case without excluding further preferred embodiments being characterized by additional features.

Figure 5:
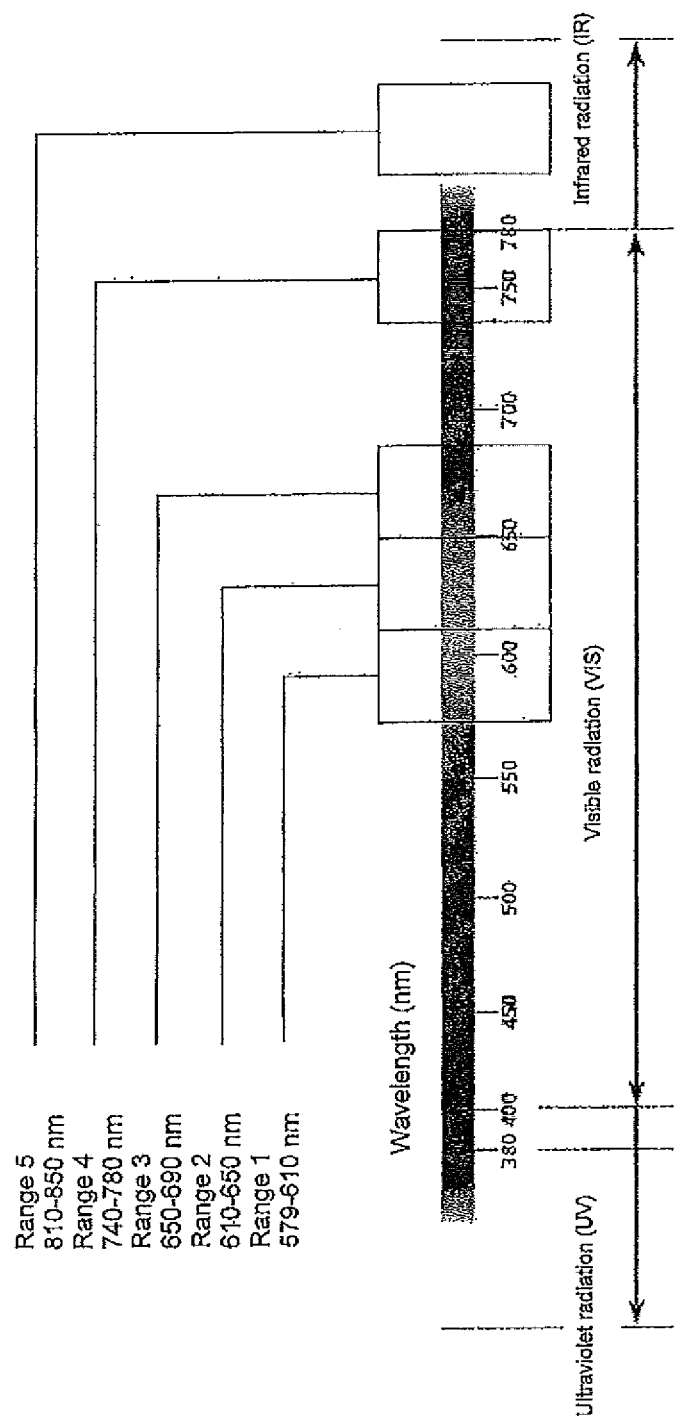
FIG. 5 shows the usual definition of the wavelength ranges of the actinic radiation spectrum in combination with five preferred emission bands of a high pressure actinic radiation-emitting lamp/reflector/filter combination in accordance with a preferred embodiment of the invention.

The term "actinic light" or "actinic radiation" as used in the present specification and the appended claims is intended to mean light or (broader) radiation of the whole electromagnetic spectrum (see the definition given below with reference to "Römpp Chemie-Lexikon" and FIG. 5 of this application) which has a photochemical (including a photobiochemical) effect and includes, as the case may be, light/ra-diation of natural or artificial origin. In the claims and specification, "actinic light" or "actinic radiation" is mainly, but not restrictively, used for light or radiation of artificial origin.

The device which is used in the present invention for the purpose of irradiating actinic radiation of at least one wavelength being in the visible range is a usual irradiation device described in the Applicants' earlier patent applications. Reference is, in this respect, made to DE 10 2005 030 388 and EP 2 055 349, mentioned above. As already mentioned above, the devices of the invention may be selected from devices for irradiating the subject's, or user's, body while the user's body is in a horizontal position, which devices, for obvious reasons, are often also called "beds", and devices for irradiating the subject's, or user's, body while the body is in a vertical position, which position may be a sitting or standing position. Both groups of irradiation devices are included in the present invention. The devices of the invention may also include irradiation devices which provide the actinic radiation to parts of the user's body only, e.g. face irradiation devices, devices irradiating the upper part of the body only, devices irradiating the chest only, devices irradiating the arms only, etc. All these devices are subsequently referred to generally as "irradiation devices" or "devices".

The devices for irradiating the user's body as useable for the purposes of the invention may have the construction known to a person skilled in this technical field. The invention is described below, for exemplary purposes and in order to allow a better understanding of the invention, by means of an irradiating device for a horizontal positioning of the user during the irradiation phase, which devices are usually called "beds" (as known for "tanning beds" in case of prior art devices emitting tanning UV radiation). The invention is, however, not restricted to bed-like irradiation devices.

The devices provided according to the present invention are not limited in their general embodiment or in their preferred embodiments to implementation with a particular type or a particular make of actinic light irradiator for irradiating the human body, but rather may be put to general use.

The terms "actinic light irradiator" or "irradiating apparatus" or "irradiating device" are understood in the following description and in the claims to mean apparatuses with which the body of a subject or user, conventionally of a person, is irradiated by means of actinic radiation. In certain embodiments of the invention which are describe below in detail, such step or irradiating may include (but, in accordance with the invention, not exclusively consist of) an irradiation step by actinic radiation which contains tanning UV radiation.

The actinic radiation is emitted by suitable radiation sources, depending upon the wavelength of such radiation, for example by suitably pressurized tubes or radiation emitters (low pressure radiation emitters, high pressure radiation emitters) or actinic radiation-emitting LEDs, onto the human body or at least parts thereof. Preferred embodiments of actinic radiation-emitting radiation sources are described below. Irradiation apparatuses or devices include those apparatuses or devices which serve to irradiate the entire body of a user and those which serve to irradiate parts of the human body (for example face irradiation apparatuses or upper body apparatuses or devices), and also those which serve to irradiate the entire body of a user and comprise additional devices (such as for example additional burners and/or tubes and/or LEDs), with which individual parts of the body (e.g. the face, the shoulders, the sides) may additionally be irradiated with actinic radiation at the same time as the user's entire body is irradiated. Particularly preferred irradiation apparatuses/devices according to the invention are whole body irradiation apparatuses/devices, of which those whole body irradiation apparatuses are still more preferred which comprise additional devices for targeted irradiation of particular body parts, for example irradiating the face and/or the shoulders.

Irradiation apparatuses of the above-described type are known from the prior art as tanning apparatuses and are described therein in detail. Reference may be made, for example, to a detailed description to the above-mentioned DE 10 2005 030 388 A and EP 2 055 349 A.

Such irradiation devices comprise elements for allowing the user/person/subject to stand on a stand, sit on a seat or lie on a bed in a position allowing said actinic radiation to impinge on at least a part of the body of said user/person/subject while on the stand, seat or bed.

A preferred embodiment is an irradiation apparatus or device conventional in the prior art and provided for tanning, or more generally: for irradiating, by actinic radiation, the user when recumbent. The invention is described below by referring mainly to such a generic irradiation device for irradiating a used when recumbent. However, the invention is not limited to such apparatuses, but rather may in principle also be provided for apparatuses in/on which a user is irradiated in the sitting or in semi-recumbent or crouching or standing position.

Such generic irradiation apparatuses preferably provided for tanning in a recumbent position conventionally comprise a stationary lower part, which, in addition to the actinic radiation source part, comprises the electrical units, switching devices and connecting devices needed for operation of the apparatus and optionally also further devices such as for example a cooling system or a ventilation system or devices for multimedia provision, and a mobile upper part. To assist the user to position him/herself on or in the irradiation apparatus, said mobile upper part is at least partially removed from the stationary lower part using suitable devices, for example by tilting or swivelling into an open position about joints or hinges, which generally (but not limiting) connect one of the longitudinal sides of the lower part movably to one of the longitudinal sides of the upper part. The mobile upper part is returned to its original position once the user has taken up his/her position, whereby a (for example) tunnel-shaped irradiation chamber is formed around the user. Alternatively, the upper part may be lifted or swivelled away from the lower part by a separate suspension and may be lowered or swivelled back towards the lower part once the user has taken up his/her position on the lower part. The same process takes place in reverse after completion of the irradiation process.

For the user of the irradiation apparatus to lie down during the process of being irradiated with actinic radiation, the stationary lower part comprises a lying surface which is permeable at least to the irradiated actinic radiation and generally (but not limiting) largely transparent. This surface comprises a material permeable at least to radiation emitted by the actinic light sources. This may be any material known to a person skilled in the art which is largely transparent to the relevant actinic radiation radiation. This material not only has the necessary transparency for the desired fractions of the radiation, but instead also displays further advantageous characteristics, such as for example sufficient stability and flexibility to bear the person to be irradiated and excellent resistance against the action of cleaning and disinfecting substances, which have to be used after the irradiation process. An acrylic polymer is advantageously used.

Below the lying surface there is arranged, preferably in the longitudinal direction of the apparatus, at least one set of radiation sources for desired radiation, in particular for actinic light radiation, particularly preferably high pressure or low pressure lamp tubes emitting such radiation having the relevant wavelengths, but conceivably also radiation-emitting LEDs. The radiation is directed, as prescribed, in the direction of the upper part of the apparatus or device and, thus, in the direction of the user recumbent on the lying surface of the apparatus, or at least at a part of his/her body or a plurality of parts of his/her body. Optionally, it is possible, in addition to the stated lamp tubes, to also arrange one or more further radiation sources in the lower part of the apparatus, these further sources ensuring targeted irradiation of particular areas of the user's body.

The upper part of the irradiation apparatus connected as described above to the stationary lower part and cooperating therewith comprises a protective surface for the user which is substantially permeable at least to relevant radiation, which protective surface is arranged between the user and the electrically operated units of the upper part. This protective surface comprise any desired material known to a person skilled in the art on the basis of his/her specialist knowledge which is substantially permeable at least to actinic radiation and is sufficiently stable. Preferably, an acrylic polymer is used for the protective surface, as is also used for the lying surface of the lower part. In a preferred embodiment, the protective surface is shaped in such a way that a (for example, but not limiting) tunnel-shaped tanning chamber is formed over the user of the irradiation apparatus recumbent under the protective surface, the highest part of the tunnel preferably lying approximately in the middle of the upper part.

Above the protective surface (preferably forming a tunnel-shaped irradiation chamber) there usually is arranged at least one set of radiation sources for actinic radiation, preferably arranged in the longitudinal direction of the apparatus. The arrangement of the actinic radiation sources in the upper part of the device takes account of the preferred (from the standpoint of the actinic radiation source) convex shape of the protective surface. The actinic radiation sources are in most cases actinic radiation-emitting high pressure or low pressure lamp tubes, but may also be other radiation sources familiar to a person skilled in the art, such as for example actinic radiation-emitting LEDs. The radiation is directed, as prescribed, in the direction of the lower part of the irradiation apparatus and thus of the user recumbent on the lying surface of the device, or at least at a part of his/her body or a plurality of parts of his/her body. In addition to the stated lamp tubes, it may be possible for one or more further radiation sources also to be arranged in the upper part of the irradiation apparatus, these being directed specifically at particular parts of the user's body, such as for example at the user's face and ensuring targeted irradiation with the desired actinic radiation.

In preferred embodiments of the invention, the actinic radiation-emitting radiation source may be selected from low pressure lamps or tubes (often containing fluorescent phosphors as layers applied to their inner surface), medium or high pressure lamps or lamp tubes (often containing certain chemical elements activated by electric voltage) and LEDs (light emitting diodes). All these actinic radiation emitting radiation sources are per se well known to a skilled person and may be selected in accordance with the requirements, e.g. the wavelength or wavelength range desired to be emitted by the respective source.

Figure 6:
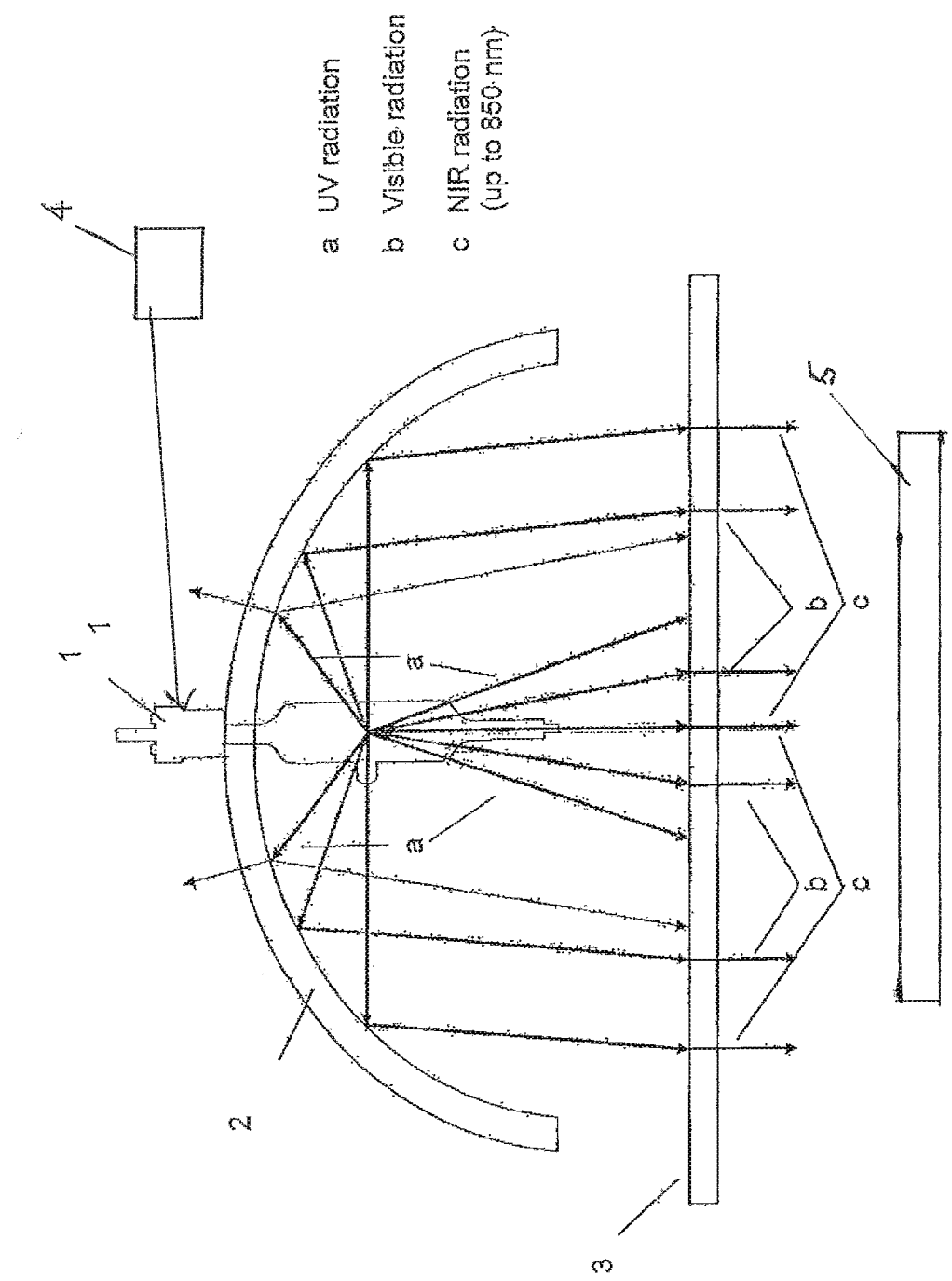
FIG. 6 shows a high pressure actinic radiation-emitting lamp/reflector/filter combination in accordance with a preferred embodiment of the invention.

A particularly preferred embodiment of actinic radiation-emitting radiation sources, which may be used in the devices of the present invention, is shown in FIG. 6. The radiation source used in preferred devices of the present invention comprises a high pressure lamp 1 emitting a certain actinic radiation spectrum, in combination with a reflector 2 surrounding the emission area of the lamp 1 and (at least partially) absorbing but mainly reflecting the light received from the lamp 1 in a certain actinic radiation range. This is achieved by a plurality of layers of radiation wavelength-securing material applied on the reflecting inner 21 surface of the reflector 2, as can be seen from the arrows a, b and c meaning UV light radiation (a), visible light radiation (b) and near-infrared (NIR) light radiation (c) which has, in accordance with the invention, a wavelength of less than or equal to 850 nm. The radiation reflected by the reflector 2 is passing a filter 3, which, in a preferred embodiment of the present invention, has a disk shape. FIG. 6 also schematically shows an element 4 which allows the control of one or more of the intensity, irradiance, dose, and time of irradiation of the actinic radiation to be irradiated and/or irradiated onto the body of a person and an element 5 which allows a person to stand on a stand, sit on a seat or lie on a bed in a position allowing actinic radiation to impinge on at least a part of the body of said person while on the stand, seat or bed.

Generally, lamp 1, reflector 2 and filter 3 are adapted to their respective wavelength ranges of emission (lamp 1), reflection (reflector 2) and radiation-filtering capability (filter 3). By a suitable selection of the properties these three parts of the radiation-emitting means of the device of the present invention, the delivery of a suitable actinic radiation having wavelengths in the desired physiologically effective range of wavelength of the visible and non-visible actinic radiation range to the body of the person/subject using the device may be reliably secured.

Figure 4:
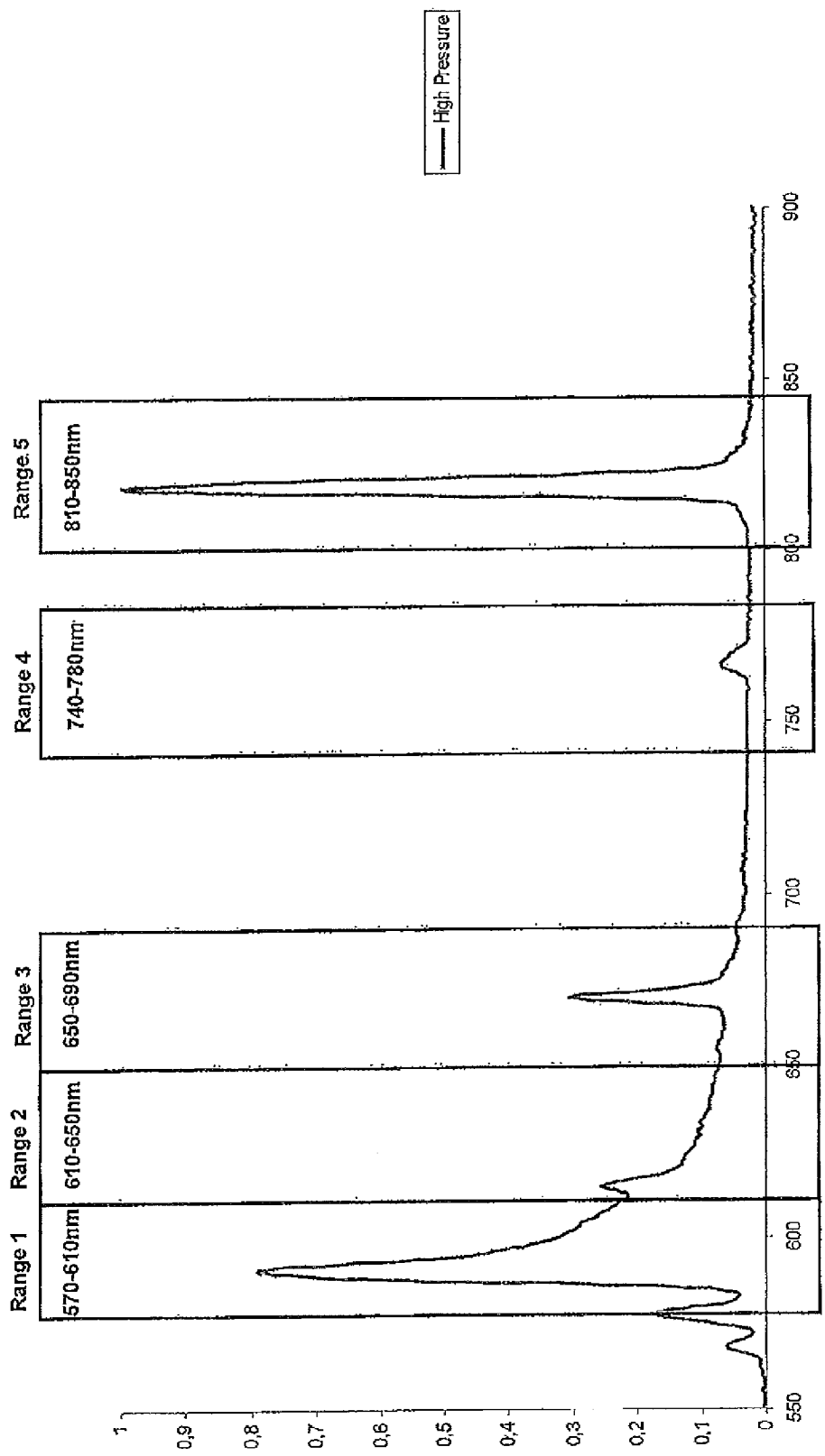
FIG. 4 shows the preferred effective wavelength ranges of the device of the present invention, in combination with the emission spectrum of a high pressure actinic radiation-emitting lamp/reflector/filter combination in accordance with a preferred embodiment of the invention.

In a more preferred embodiment of the device of the present invention, the emission spectrum of the lamp 1 (which preferable is a high pressure lamp) covers an actinic radiation wavelength range from the close UV range of wavelengths over the visible range of wavelengths to the close IR range of wavelengths. In more preferred embodiments of the device of the present invention, the emission spectrum of the lamp 1 covers an actinic radiation wavelength range comprising at least a part of the visible range of wavelengths and a part of the close IR range of wavelengths. Even more preferred in accordance with the invention are devices where the high pressure lamp 1 covers wavelengths between 570 nm and 850 nm, in which range several, preferably five, sub-ranges may be defined which are exemplarily shown in FIG. 4. In even more preferred embodiments of the device of the invention, the sub-ranges of the actinic radiation emission of the (preferably) high-pressure lamp 1 may have central peak wavelengths of, for example, approximately 590 nm (in the 570 to 620 nm visible range), approximately 630 nm (in the 610 to 650 nm visible range), approximately 670 nm (in the 650 to 690 nm visible range), approximately 760 nm (in the 740 to 780 nm visible range) and approximately 830 nm (in the 810 to 850 nm non-visible range).

In a further preferred embodiment of the device of the present invention, the actinic radiation emitted by the lamp 1 (preferably in the above-mentioned wavelength ranges) is reflected by an appropriately arranged reflector 2. The reflector 2 is preferably capable to reflect the actinic radiation emitted by the lamp 1 towards the user (as will be described in detail below: through a suitable filter 3). In a more preferred embodiment of the device of the invention, the reflector is a reflector having a coating on its inner (convex) side 21. Such a coating appropriately refracts the light coming in from the lamp 1. In further preferred embodiments, the coating is a dielectric coating made of several (for example from 20 to 50, more preferably 30 to 45) layers. In accordance with particularly preferred embodiments of the device of the invention, but without restriction to such an embodiment, an arrangement of (for example 37 or 39 or 41) layers of titanium dioxide ($TiO_2$) and silicon dioxide ($SiO_2$) resulting into an overall thickness in the range of from 1 to 10 µm, for example an overall thickness of approximately 4 µm, has turned out to be beneficial as a coating of the convex inner side 21 of the reflector 2. Such a coating, for example, results into spectral properties having the following characteristic data (to which, however, the invention is not restricted) (R is the reflection (in %); "avg" means "average"):

$R_{avg}$>95%@about 580 to about 850 nm;
$R_{avg}$<15%@about 950 to 2500 nm;
AOI=54°.

In other words: The major amount of reflected light (>95%) has a wavelength in the range of from about 580 to about 850 nm. Hence, by the properties of the reflector 2 of the preferred device of the present invention, the broader range of emitted actinic radiation coming from the lamp 1 is "cut down" to the wavelength range of (predominantly) about 580 to about 850 nm, without, however, completely removing actinic radiation in shorter and longer wavelength ranges. The reflection spectrum of the preferred reflector 2 of the device of the present invention is shown in FIG. 1.

In another preferred embodiment of the device of the present invention, there is included into the lamp/reflector/filter combination a filter 3 through which the actinic radiation reflected by the reflector 2 has to pass before it is impinging onto the user's body. In a particularly preferred embodiment of the device of the present invention, the final wavelength range comprising at least one visible wavelength range, and in an even more preferred embodiment comprising also one non-visible wavelength range, is generated by filtering, out of the ranges guided to the filter 3 by the reflector 2, only particularly beneficial (i.e. physiologically effective and having a beneficial effect to the user's body) wavelengths of the actinic radiation.

Figure 2:
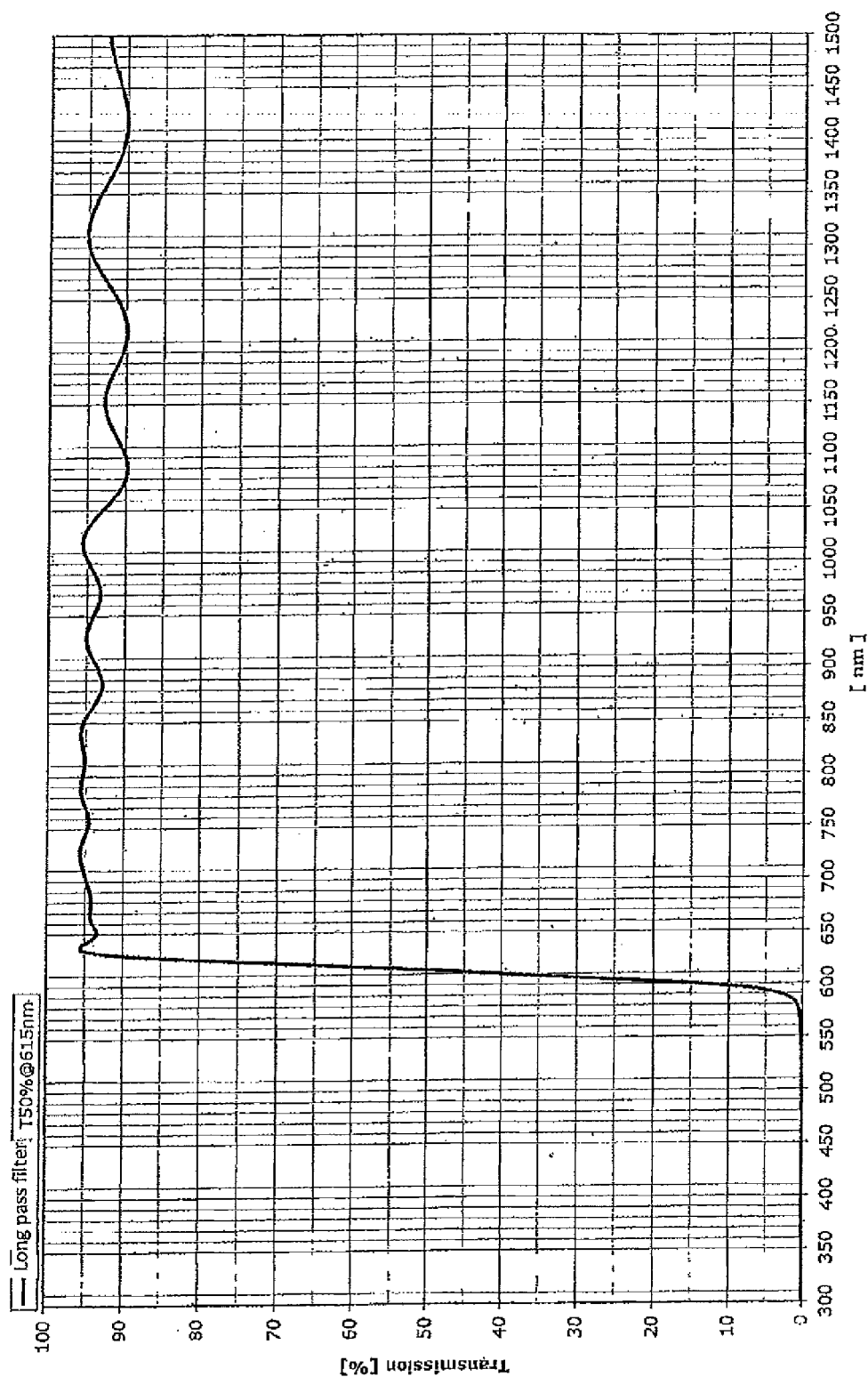
FIG. 2 shows an actinic light transmission spectrum (capable of preventing short wavelength actinic light (<570 nm) from passing and allowing long wavelength actinic light (≥570 nm) to pass) of a preferred actinic light-emitting high pressure lamp/reflector/filter combination in accordance with a preferred embodiment of the invention.

This is achieved, in a more preferred embodiment of the device of the invention, by a filter having a transmission spectrum shown in FIG. 2. In other words: Such a filter 2

(called "filter passing long wavelengths"="Langpass-Filter") completely "cuts down" the (dangerous) short (e.g. UV) wavelengths of the actinic radiation which may have been emitted by the lamp 1 and have been reflected by the reflector 2 so that only light may pass the filter the wavelengths of which are above about 570 nm.

In more preferred embodiments, such a filter allowing the transmission of actinic radiation having wavelengths ≥about 570 nm may have the following characteristic data (also called "filter performance characteristics") (T is the transmission of light (in %); "avg" means "average"):

$T_{avg}$>85%@about 650 to about 850 nm;
$T_1$=50%@about 610±10 nm;
$T_{avg}$<1%@<about 570 nm.

According to an even more preferred embodiment of the device of the present invention, such a filter may comprise a transparent filter material commonly used for the present purposes, on which a dielectric coating system is preferably deposited. Such a coating may be a dielectric coating made of several (for example from about 20 to about 50, more preferably about 30 to about 45) layers. In accordance with particularly preferred embodiments of the device of the invention, but without restriction to such an embodiment, an arrangement of (for example 34 or 36 or 38) alternatively deposited layers of (highly refractive) titanium dioxide ($TiO_2$) and (low refractive) silicon dioxide ($SiO_2$) resulting into an overall thickness in the range of from about 1 to about 5 μm, for example an overall thickness of about 2 to about 3 μm, has turned out to be beneficial as a coating of the filter 3.

In other words: The major amount of light (>about 85%) having passed the filter 3 has a wavelength in the range of ≥about 570 nm. Hence, by the properties of the filter 3 of the preferred device of the present invention, the broader range of emitted actinic radiation coming from the reflector 2 is "cut down" to actinic radiation having wavelengths range of (predominantly) ≥about 570 nm. Actinic radiation having longer wavelength ranges come from the reflector 2 only in minor amounts (see FIG. 1). The transmission spectrum of the preferred filter 3 of the device of the present invention is shown in FIG. 2.

In accordance with a further preferred embodiment of the device of the invention, the filter 3 of the lamp/reflector/filter combination, through which the actinic radiation reflected by the reflector 2 has to pass before it is impinging onto the user's body is capable of generating a final wavelength range comprising at least one visible wavelength range, and in an even more preferred embodiment comprising also one non-visible wavelength range, by filtering, out of the ranges guided to the filter 3 by the reflector 2, particularly beneficial (i.e. physiologically effective and having a beneficial effect to the user's body) wavelengths of the actinic radiation in such a way that not only completely "cuts down" the (dangerous) short (e.g. UV) wavelengths of the actinic radiation which may have been emitted by the lamp 1 and have been reflected by the reflector 2, but also substantially "cuts down" the long wavelengths exceeding about 850 nm and, in particular those exceeding 1100 nm. Such a filter sometimes is called a "filter passing short wavelengths" or "Kurzpass-Filter". As a result, the actinic radiation passing the filter has wavelengths in the range of from about 570 nm and substantially not exceeding about 850 nm.

In more preferred embodiments, such a filter allowing the transmission of actinic radiation having wavelengths about 570 nm may substantially not exceeding 850 nm have the following characteristic data (also called "filter performance characteristics") (T is the transmission of light (in %); "avg" means "average"):

$T_{avg}$<15%@about 1100 to about 2500 nm;
$T_2$=50%@about 900±20 nm;
$T_{avg}$>85%@about 650 to about 850 nm;
$T_1$=50%@about 610±10 nm;
$T_{avg}$>1%@<about 570 nm.

According to an even more preferred embodiment of the device of the present invention, such a filter may comprise a transparent filter material commonly used for the present purposes, on which several coatings are preferably applied, such coatings more preferably comprising a dielectric coating made of several (for example from about 20 to about 50, more preferably about 30 to about 45) layers, more preferably in the form of an arrangement of (for example 34 or 36 or 38) alternatively deposited layers of (highly refractive) titanium dioxide ($TiO_2$) and (low refractive) silicon dioxide ($SiO_2$) resulting into an overall thickness in the range of from about 1 to about 5 μm, for example an overall thickness of about 2 to about 3 μm, which coating is for cutting down the short wavelength actinic radiation, and comprising a coating of indium tin oxide and a dielectric coating made of several (for example from about 10 to about 30, more preferably about 15 to about 20) layers, more preferably in the form of an arrangement of (for example 16 or 18 or 20) alternatively deposited layers of (highly refractive) tantalum pentoxide ($Ta_2O_5$) and (low refractive) silicon dioxide ($SiO_2$) resulting into an overall thickness in the range of from about 1 to about 5 μm, for example an overall thickness of from about 2 to about 3 μm, which coating is for cutting down the long wavelength actinic radiation.

Figure 3:
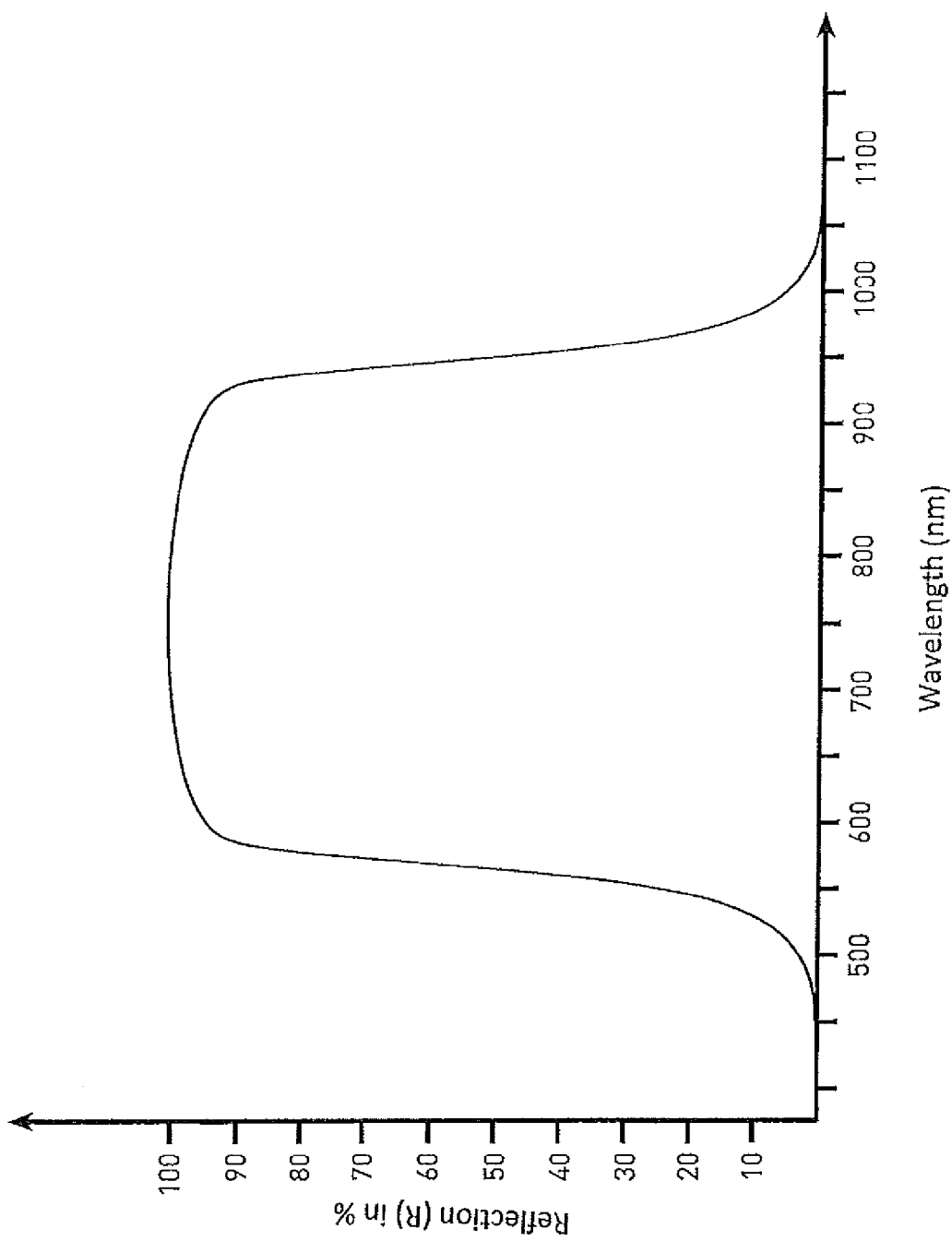
FIG. 3 shows an actinic light transmission spectrum (capable of preventing short wavelength actinic light (<570 nm) and long wavelength actinic light (>850 nm) from passing and allowing actinic light only in a wavelength range of from approximately ≥570 nm to ≤850 nm to pass) of a preferred actinic light-emitting high pressure lamp/reflector/filter combination in accordance with a preferred embodiment of the invention.

In other words: The major amount of light (>about 85%) having passed the filter 3 has a wavelength in the range of from ≥about 570 nm. In addition, only small amounts of actinic radiation having wavelengths exceeding about 850 nm passes the filter 3. Hence, by the properties of the filter 3 of the preferred device of the present invention, the broader range of emitted actinic radiation coming from the reflector 2 is "cut down" to actinic radiation having wavelengths range of (predominantly) ≥about 570 nm. Actinic radiation having longer wavelength ranges come from the reflector 2 only in minor amounts (see FIG. 1), and these are also "cut down" by the present filter 3. The transmission spectrum of the latter filter 3 of the device of the present invention is shown in FIG. 3.

The latter embodiment, albeit excellent in its properties of providing actinic radiation beneficial for the user's body, is presently less preferred, compared to the one where only the long wavelength actinic radiation is passed, due to the relatively high economic input for the filter coatings cutting down the long wavelength actinic radiation.

In preferred embodiments of the device of the present invention, the above-described combinations of lamp 1, reflector 2 and filter 3 may be used beneficially in any suitable amount, which may be selected by a skilled person in accordance with the requirements either alone or in combination with other means for emitting actinic radiation. More preferred are devices of the invention which make use of such lamp/reflector/filter combinations exclusively. Their number in the preferred devices of the invention may depend upon the size and purpose of the irradiation devices: Smaller ones (for irradiating the user's body only partially, e.g. the face, the arms, the upper body, the chest) may comprise only a few of such lamp/reflector/filter combinations, e.g. about 3 (for a face irradiator) or about 3 to about 6 (for a partial body irradiator), while others may appropriately require about 10 to about 50, preferably about 15 to about 30, combinations, or even less or even more, depending upon their size (for a full body irradiator). A skilled person may select the appropriate number according to the purpose, based on the requirement that the user's body (or the relevant part of the user's body) should be completely and appropriately irradiated with the suitable wavelength actinic radiation from all sides in order to achieve the beneficial medical and/or cosmetic result.

Irradiation apparatuses for applying a user with actinic radiation when standing or sitting are constructed in accordance with the user's other than recumbent position, but substantially comprise the same components essential for irradiation with actinic radiation as the above-described apparatus for receiving actinic radiation in the recumbent position, which is preferred according to the invention.

Such a per se known irradiation apparatus comprises, in accordance with the present invention, further devices useful or advisable for irradiation of a user's body. These are means (elements) allowing a control of the intensity, irradiance, dose, and/or time of irradiation of said actinic radiation to be irradiated and/or irradiated onto the body of said user/person/subject. Such means are described in detail in the above-mentioned EP 2 055 349 A. Such means (elements) which subsequently is referred to by the term "means for safeguarding the spectral distribution of actinic radiation emitted by actinic radiation sources in apparatuses for irradiating the human body with actinic radiation" will now be further described in connection with the present invention.

Without limitation such means for safeguarding the spectral distribution of actinic radiation emitted by actinic radiation sources in apparatuses/devices for irradiating the human body with actinic radiation may comprise one means alone or two or more or all means in combination, selected from or combined from the following:

means (elements) for ensuring non-interchangeable connection of only those radiation sources whose spectral distribution and dose of the emitted actinic radiation, thanks to their construction, permit compliance with the limit value for regulated erythemally effective irradiance; which means preferably are the means for ensuring non-interchangeable connection of radiation sources in the form of mechanical safeguarding means, preferably means for ensuring non-interchangeable connection of radiation sources in the form of safeguarding means associated with the shape of the connection or in which the means for ensuring non-interchangeable connection of radiation sources are safeguarding means associated with tube length; or alternatively which means are electrical and/or electronic safeguarding means, preferably in the form of means for ensuring non-interchangeable connection of radiation sources by outputting and/or detecting an electronic code of the radiation sources used; or alternatively means which are a combination of mechanical and electr(on)ic safeguarding means;

means (elements) for varying the spectral distribution of ultraviolet radiation emitted by actinic radiation sources; which means preferably are means for varying how the actinic radiation irradiator is equipped with radiation sources with primarily actinic radiation emission of a first type A and with radiation sources with primarily actinic radiation emission of a second type B, so establishing a variable ratio of type A radiation/type B radiation, preferably in which the means for varying the spectral distribution of actinic radiation emitted by type A radiation sources are means for adjusting the quantity of emitted type A radiation from the type A/type B spectral ranges, more preferably in which the means for varying the spectral distribution of actinic radiation emitted by actinic radiation sources are means for adjusting the quantity of emitted actinic radiation from the type A/type B radiation ranges to a value in a certain range; in preferred embodiments, such an adjustment is effected by a control of the number of actinic radiation sources primarily emitting type A radiation relative to the number actinic radiation sources primarily emitting a different actinic radiation, for example a type B radiation, or is effected by a control of electrical activation of the actinic radiation sources primarily emitting type A radiation relative to the electrical activation of the actinic radiation sources primarily emitting a different actinic radiation, for example a type B radiation; even more preferably, such a control of the electrical activation takes place by switching on and off radiation sources primarily emitting a given actinic radiation, or such a control of the electrical activation takes place by dimming radiation sources primarily emitting a given actinic radiation;

means (elements) for automatic adjustment of the values of emitted actinic radiation doses of a spectral distribution of actinic radiation emitted by actinic radiation sources in accordance with the results from a measurement of the skin type and/or skin status of a person to be irradiated; in this connection, the term "automatic adjustment" means that the results of the measurement are directly and without any further intermediate step used for adjusting the amount or dose or radiance of actinic radiation emitted by the actinic radiation sources; such means may preferably be means for automatic adjustment of maximum values for emitted actinic radiation doses, means for adjusting values for emitted actinic radiation doses per predetermined unit time, means for adjusting values for maximum irradiation time with a predetermined, time-related actinic radiation dose and/or means for adjusting other irradiation-relevant parameters; for achieving such values used for the automatic adjustment, the measurement(s) of the skin type and/or of the skin status of a person to be irradiated proceed optically; preferably the measurement(s) of the skin type and/or of the skin status of a person to be irradiated proceed by means of light measurement using light of at least two different wavelengths; more preferably the measurement(s) of the skin type and/or of the skin status of a person to be irradiated proceed by means of light from at least two LEDs with different emission wavelengths;

means (elements) for detecting the actinic radiation dose actually emitted over the entire actinic radiation spectral range in the area, and/or over the time, of actual impingement thereof on the irradiated human body (actual data) and means for comparison with predetermined nominal data and optionally means for automatically limiting the actinic radiation dose and/or the irradiation time, which means preferably may be means for summary detection of the radiation dose actually emitted by all the actinic radiation sources over the entire actinic radiation spectral range and more preferably may be actinic radiation sensors for the relevant wavelength range of the actinic radiation.

In accordance with the present invention, the above means (elements) allowing a control of the intensity, dose, and/or time of irradiation of said actinic radiation comprises a means for determining the skin status, preferably the skin tan status, and/or the skin type of the person to be irradiated with said actinic radiation. Means for determining the skin status and/or skin type of the person to be irradiated by actinic radiation are known to a skilled person from the prior art. One example for a disclosure of such a means for determining the skin status and/or skin type of the person to be irradiated by actinic radiation is known from the EP 1 508 301 A, the entire disclosure of which is incorporated by reference herein.

In a preferred embodiment of the present invention, the means (elements) of allowing a control of the intensity, dose, and/or time of irradiation of said actinic radiation delivers a result directly from the measurement of the skin status and/or the skin type of the person to be irradiated and/or irradiated to effect a control of the intensity, irradiance, dose, and/or time of irradiation of said actinic radiation. In this context, the direct provision of the measurement result of the skin status and/or the skin type of the person to be irradiated and/or irradiated for a direct control of the intensity, irradiance, dose, and/or time of irradiation of said actinic radiation means that the results of the measurement are directly and without any further intermediate step used for adjusting the amount or dose or radiance of actinic radiation emitted by the actinic radiation source or sources.

In accordance with the present invention, the device for irradiating a body of a person/user/subject with actinic radiation of at least two different wavelengths having at least one physiological effect on the body of said person/user/subject comprises means (elements) comprising one or more sources of radiation, said sources of radiation emitting radiation of at least two different wavelengths having at least one physiological effect on the body of said person/user/subject. Of such one or more radiation wavelengths, at least one is in the visible range, and said radiation of the at least two different wavelengths is directed to at least a part of the body of said person.

In accordance with the invention, the device of the invention comprises at least one source of actinic radiation. Hence, the device may comprise one source of actinic radiation or two or more sources of actinic radiation. The source(s) of actinic radiation, as mentioned above, may for example be low pressure lamps or may be high pressure lamps or may be LEDs. In addition, the source(s) of actinic radiation may each emit one specific wavelength (as, for example, a LED), or the source(s) of radiation may emit several different wavelengths or different wavelength bands or even a spectrum of actinic radiation extending over a broad wavelength range, by which the actinic radiation of the at least two wavelengths emitted in accordance with the invention are covered.

In accordance with the invention, the at least two wavelengths emitted may have at least one physiological effect on the body of the user/person/subject who is receiving the actinic radiation. There may be exerted one physiological effect on the body of the user treated by the actinic radiation, or there may be exerted several physiological effects on the body of the user/person/subject receiving the actinic radiation. One physiological effect or two physiological effects are preferred in accordance with the present invention.

In accordance with the present invention, at least one of the wavelengths emitted by the actinic radiation sources of the device of the invention are in the visible range of actinic radiation. In accordance with the general definition, the "visible range" of wavelengths of the actinic radiation is defined for the present invention to be the wavelength range between 400 and 800 nm (Römpp Lexikon der Chemie, Keyword "Spektroskopie", 10$^{th}$ Edition, Thieme Publishers); see also FIG. 5.

In a preferred embodiment of the invention, the radiation of at least one wavelength emitted by the actinic radiation source (s) of the device of the invention is in the range of visible wavelengths, and the radiation of at least one different wavelength is in the range of non-visible wavelengths. In accordance with the general definition already addressed above, the "visible range" of wavelengths of the actinic radiation is defined for the present invention as given above, and the "non-visible range" of wavelengths of the actinic radiation is defined for the present invention to be the wavelength range below 400 nm and the wavelength range above 800 nm (Römpp Lexikon der Chemie, loc cit., and FIG. 5).

In further preferred embodiments of the invention which result into beneficial physiological effects in accordance with the present invention, the radiation of the at least one wavelength in the range of non-visible wavelengths is radiation of a wavelength selected from about 810 to about 850 nm, more preferably radiation of a wavelength selected from about 820 to about 840 nm for example a wavelength of about 830 nm.

In an alternative preferred embodiment of the present invention which may be realized alone or may be realized together, i.e. in combination, with the previously mentioned preferred embodiment, the radiation of at the least one wavelength in the range of visible wavelengths is radiation of a wavelength selected from about 570 to about 780 nm, preferably of a wavelength selected from the ranges of from about 570 nm to about 610 nm (more preferably of about 590 nm), of from about 610 nm to about 650 nm (more preferably of about 630 nm), of from about 650 to about 690 nm (more preferably of about 670 nm), and of from about 740 to about 780 nm (more preferably of about 760 nm). A device irradiating the body of a user/person/subject with combinations of actinic radiation in these wavelength ranges of visible and non-visible actinic radiation results into particularly beneficial physiological effects which are described in detail below.

In further preferred embodiments of the present invention, at least one radiation of the at least one wavelength emitted by the at least one source of radiation, and more preferably two wavelengths radiations of the above preferred radiations in the visible and in the non-visible wavelength range, is/are emitted in a narrow wavelength band or in two narrow wavelength bands. Even more preferably, such actinic radiation of one or two wavelengths in the visible and in the non-visible actinic radiation range of wavelengths is/are emitted by at least one type of low pressure lamp and more preferably is/are emitted by at least one type of Light Emitting Diode (LED) and/or by at least one type of low-pressure tube lamps containing at least one light-emitting phosphor, for each of the different radiations in said two wavelengths ranges of the visible and non-visible ranges mentioned above. The results are particularly beneficial physiological effects exerted on the body of the person/user/subject receiving such combined radiation.

In an alternative, albeit preferred embodiment of the device of the present invention, at least one radiation of the at least one wavelength emitted by the at least one source of radiation, and more preferably two wavelengths radiations of the above preferred radiations in the visible and in the non-visible wavelength range, is/are emitted in a broad wavelength band and preferably is/are emitted by at least one type of high pressure lamp and even more preferably is/are emitted by at least one type of high-pressure discharge lamp. Also in this case, beneficial physiological effects are exerted on the body of the person/user/subject receiving such combined radiation of actinic light sources emitting such light.

Particularly in the latter case, it is—due to the beneficial effects exerted on the body of the user receiving the actinic radiation—a further preferred embodiment of the device of the present invention that such a device further comprises a filter allowing the passage of radiation of at least one well-defined wavelength band. Such a filter is—in general—well known to a person skilled in the present field and may be selected by a skilled person in accordance with the requirements, e.g. in accordance with the wavelength range or specific wavelengths which has to be irradiated onto the body of a user of the device. In embodiments further preferred due to their beneficial effect of the radiation passed by the filter and impinging onto the body of the user of the device, such a filter preferably allows the passage of actinic radiation of a wavelength band in the range of from about 570 to about 780 nm, preferably of a wavelength selected from the ranges of from about 570 nm to about 610 nm (more preferably of about 590 nm), of from about 610 nm to about 650 nm (more preferably of about 630 nm), of from about 650 to about 690 nm (more preferably of about 670 nm), and of from about 740 to about 780 nm (more preferably of about 760 nm), in the visible range of actinic radiation.

In an alternative preferred embodiment of the present invention which may be realized alone or may be realized together, i.e., in combination, with the previously mentioned preferred embodiment, the filter allowing a passage of radiation of at the least one wavelength in the range of non-visible wavelengths is a filter allowing the passage of radiation preferably of a wavelength band in the range of from about 810 to about 850 nm, more preferably in the range of from about 820 to about 840 nm, for example at approximately about 830 nm.

Such filters preferable useable in the devices of the present invention are, per se, also known to a skilled person and may be selected by a skilled person in accordance with the requirements. Their use in a combination of actinic light-emitting lamp, reflector and filter was in detail described above.

In preferred embodiments of the invention, the device of the invention, particularly in the above preferred embodiment, employs a filter—or two or more filters—allowing the passage of radiation within a range of wavelengths v, wherein v is defined by v≥about 570 nm. In other words, the filter(s) employed in the device operated with actinic radiation sources covering a larger range of wavelengths allow(s) the passage of actinic radiation to the body of a user of the device which filter(s) cut(s) away the wavelengths shorter than about 570 nm and allow(s) a passage of actinic radiation having a wavelength v≥about 570 nm. Even more preferred is a device of the invention in which a filter—or several filters—is/are employed wherein v is defined by about 570 nm≤v≤about 950 nm. This means that the filter(s) employed in the device operated with actinic radiation sources covering a larger range of wavelengths allow(s) the passage of actinic radiation to the body of a user of the device which filter(s) cut(s) away the wavelengths longer than about 950 nm and shorter than about 570 nm and allow(s) a passage of actinic radiation having a wavelength in the range of about 570 nm≤v≤about 950 nm.

In accordance with even more preferred embodiments of the device of the invention, the device employs one filter or several filters in combination with actinic radiation sources covering a larger range of wavelengths (e.g. of the range of at least 500 to 1000 nm), which filter has/which filters have the following filter performance characteristics:

$T_{avg}$>85%@about 650 to about 850 nm;
$T_1$=50%@about 610±10 nm;
$T_{avg}$<1%@<about 570 nm.

It is even more preferred in accordance with the present invention that the device used for irradiating the body of a user preferably employs a filter having the following filter performance characteristics:

$T_{avg}$<15%@about 1100 to about 2500 nm;
$T_2$=50%@about 900±20 nm;
$T_{avg}$>85%@about 650 to about 850 nm;
$T_1$=50%@about 610±10 nm;
$T_{avg}$<1%@<about 570 nm.

Such filters are known to a person skilled in the present technical field and my be selected in accordance with the requirements of the present device, i.e. in accordance with the desired wavelengths or wavelength ranges of the actinic radiation to be irradiated to the user or person in order to achieve a beneficial effect. Specifically, the device—in combination with actinic radiation sources covering a larger range of wavelengths (e.g. of the range of at least about 500 to about 1000 nm)—makes use of a filter which has at least one coating allowing the passage actinic radiation of long wavelengths. More preferably, a filter is used having at least one coating selected from a coating comprising $SiO_2$ and a coating comprising $TiO_2$ and a coating comprising combinations thereof, in order to allow only such actinic radiation to pass from the actinic radiation sources to the body of the user of the device, which has a wavelength in a range above, or equal to, about 570 nm. Hence, all radiation having a wavelength below about 570 nm is cut away from the actinic radiation emitted by the actinic radiation source(s) and does not reach the user's body, when the device of this preferred embodiment of the invention is used.

Alternatively, and in even more preferred embodiments of the device of the invention, a filter is used having at least one coating allowing the passage of actinic radiation of short wavelengths and having at least one coating allowing the passage of actinic radiation of long wavelengths. This is achieved in a preferred manner by operating a device, wherein a filter is used having at least one coating selected of a coating comprising ITO (indium tin oxide), a coating comprising $SiO_2$ and a coating comprising $Ta_2O_5$ and a coating comprising combinations thereof, and at least one coating selected of a coating comprising $SiO_2$ and a coating comprising $TiO_2$ and a coating comprising combinations thereof. In these cases, not only such actinic radiation is prevented from passing the filter on the route from the actinic radiation source(s) to the body of the user of the device, which has a wavelength in a range above approximately 1000 nm, but also such actinic radiation is prevented from passing the filter on the route from the actinic radiation source(s) to the body of the user of the device, which has a wavelength in a range below approximately 570 nm.

Particularly preferred wavelength ranges of actinic radiation allowed to pass the filter on the route from the actinic radiation sources to the human body/the user's body are actinic radiation wavelengths selected, for example, from about 810 to about 850 nm, preferably of a wavelength selected from about 820 to about 840 nm, more preferably of a wavelength of about 830 nm, in the range of non-visible wavelengths and/or are actinic radiation wavelengths selected, for example, from about 570 to about 780 nm, preferably of a wavelength selected from the ranges of from about 570 nm to about 610 nm (more preferably of about 590 nm), of from about 610 nm to about 650 nm (more preferably of about 630 nm), of from about 650 to about 690 nm (more preferably of about 670 nm), and of from about 740 to about 780 nm (more preferably of about 760 nm) in the range of visible wavelengths.

In accordance with the present invention, the device for irradiating a body of a person with actinic radiation of at least two different wavelengths having at least one physiological effect (most preferably at least one beneficial physiological effect), of which at least one wavelength is in the visible range, is for a medical use, i.e. may be used for medical applications. In these cases, the above at least one physiological effect (most preferably the at least one beneficial physiological effect) on the body of the user receiving such actinic radiation is a physiological effect in the medical field.

In accordance with another embodiment of the invention, the device for irradiating a body of a person with actinic radiation of at least two different wavelengths having at least one physiological effect (most preferably at least one beneficial physiological effect), of which at least one wavelength is in the visible range, is for a cosmetic use, i.e. may be used for cosmetic applications. In these cases, the above at least one physiological effect (most preferably the at least one beneficial physiological effect) on the body of the user receiving such actinic radiation is a physiological effect in the cosmetic field.

The device of the invention for medical use may have applications, to give preferred embodiments of the invention which do not restrict the invention, for a treatment of ageing of the skin, of sunburn and/or erythema (dermatitis solaris) resulting from excessive exposition of the skin to UV radiation, in the treatment of acne, in the treatment of skin irritation, in the treatment of inflammations of the skin and in the treatment of psoriasis. The latter application is particularly surprising, since acne (and also psoriasis) was often treated by providing actinic radiation in the wavelength range of UV radiation; in accordance with the invention, a treatment of acne or psoriasis, as well as a treatment of skin irritations and inflammations of the skin, with actinic radiation in the visible (red) range and/or in the close IR range, particularly by visible light in the wavelength range of about 570 to about 780 nm, more preferably in the ranges of from about 570 nm to about 610 nm, from about 610 nm to about 650 nm, from about 650 nm to about 690 nm and/or from about 740 nm to about 780 nm and/or upon irradiation by non-visible light in the wavelength range of from about 810 nm to about 850 nm, has turned out to be beneficial and particularly could induce a long-term improvement of the diseases.

The device of the invention for cosmetic use may have applications, to give preferred embodiments of the invention which do not restrict the invention, for a treatment of ageing of the skin by causing the skin to effect collagenogenesis and/or hyaluronic acid genesis and/or elastinogenesis upon irradiation by visible light in the wavelength range of about 570 to about 780 nm, more preferably in the ranges of from about 570 nm to about 610 nm, from about 610 nm to about 650 nm, from about 650 nm to about 690 nm and/or from about 740 nm to about 780 nm and/or upon irradiation by non-visible light in the wavelength range of from about 810 nm to about 850 nm. The latter application is considered to be surprising, since a treatment of ageing of the skin was considered to be effective in the fame of a treatment of the skin by irradiation with actinic light of about 610 to about 650 nm wavelength (without substantial IR radiation content) plus accompanying irradiation of actinic light of about 280 to about 320 nm (which is the UV-B range) [Hapro utility model, loc. cit.], or by irradiation with actinic light of about 580 to about 800 nm wavelength plus accompanying irradiation of tanning actinic light of about 295 to about 400 nm (which are the UV-A and UV-B ranges) [KBL utility model, loc. cit.]. In the present invention, no actinic radiation in the UV range is needed to effect a treatment of skin ageing with collagenogenesis.

The latter cosmetic application of the device of the invention may be conducted without the application of further usual cosmetic preparations. The invention, however, is, in preferred embodiments, also directed to devices for a cosmetic use as described above in combination with usual cosmetic preparations, which in further preferred embodiments are applied to the skin of the user of the device of the invention before, during or after the radiation treatment with the purpose of a treatment of ageing of the skin.

While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A device for irradiating a body of a person with actinic radiation of at least two different wavelengths, wherein the device comprises one or more elements (A) for allowing the person to stand on a stand, sit on a seat or lie on a bed in a position allowing said actinic radiation to impinge on at least a part of a body of said person while on the stand, seat or bed, so that said radiation of the at least two different wavelengths is directed to at least a part of the body of said person;

one or more elements (B) allowing control of at least one of intensity, irradiance, dose, and time of irradiation of said actinic radiation to be irradiated and/or irradiated onto the body of said person;

one or more elements (C) comprising one or more sources of radiation selected from one or more of low pressure lamps, medium pressure lamps, high pressure lamps, and LEDs, said sources of radiation emitting radiation of at least two different radiation wavelengths having at least one physiological effect on the body of said person, at least one of said different radiation wavelengths being in a visible range and at least one of said different radiation wavelengths being in a range of non-visible wavelengths and said at least one actinic radiation emitted by said one or more sources of radiation being emitted in a broad wavelength band from the close UV range of wavelengths over the visible range of wavelengths to the close IR range of wavelengths;

a concave reflector provided with a coating on its inner side and capable of reflecting the actinic radiation emitted by said one or more sources of radiation toward said person, said coating on the inner concave side resulting in spectral characteristics (wherein "R" is reflection, "avg" means "average" and "AOI" means "angle of incidence"):

$R_{avg} > 95\%$ @580 to 850 nm;
$R_{avg} < 15\%$ @950 to 2500 nm;
AOI=54°; and a filter having the following performance characteristics (wherein "T" is transmission of light and "avg" means average):

$T_{avg} > 85\%$ @650 to 850 nm;
$T_1 = 50\%$ @610±10 nm;
$T_{avg} < 1\%$ @<570 nm;

and allowing a passage of actinic radiation of a wavelength band in a range selected from 570 nm to 610 nm, 610 nm to 650 nm, 650 nm to 690 nm, and 740 to 780 nm and combinations thereof, and allowing a passage of actinic radiation of a wavelength band in a range of from 820 nm to 840 nm.

2. The device of claim 1, wherein said one or more elements (B) comprise one or more elements for determining at least one of a skin status and a skin type of the person to be irradiated with said actinic radiation.

3. The device of claim 2, wherein a result of a determination by said one or more elements (B) allows direct control of at least one of intensity, irradiance, dose, and time of irradiation of said actinic radiation.

4. The device of claim 1, wherein the device comprises a filter having at least one coating allowing passage of actinic radiation of long wavelengths ("long wave-pass filter coating") and having at least one coating selected from a coating comprising $SiO_2$, a coating comprising $TiO_2$, and a coating comprising combinations thereof.

5. The device of claim 1, wherein the device comprises a filter having at least one coating allowing passage of actinic radiation of short wavelengths ("short wave-pass filter coating") and having at least one coating allowing passage of actinic radiation of long wavelengths ("long wave-pass filter coating") and having at least one coating selected from a coating comprising ITO (indium tin oxide), a coating comprising $SiO_2$, a coating comprising $Ta_2O_5$, and a coating comprising combinations thereof, and at least one coating selected from a coating comprising $SiO_2$, a coating comprising $TiO_2$, and a coating comprising combinations thereof.

6. The device of claim 1, wherein said filter has the following performance characteristics (wherein "T" is transmission of light and "avg" means average):

$T_{avg}<15\%$@1100 to 2500 nm;
$T_2=50\%$@900±20 nm;
$T_{avg}>85\%$@650 to 850 nm;
$T_1=50\%$@610±10 nm;
$T_{avg}<1\%$@<570 nm.

7. A medical treatment method, wherein the method comprises irradiating at least a part of a person's skin by using the device of claim 1.

8. A cosmetic treatment method, wherein the method comprises irradiating at least a part of a person's skin by using the device of claim 1.

9. A method of treating at least one of ageing skin, sunburn, erythema resulting from excessive exposition of skin to UV radiation, acne, skin irritation, inflammation of skin, and psoriasis, wherein the method comprises irradiating at least a part of affected skin by using the device of claim 1.

10. A method of treating ageing skin by causing the skin to effect collagenogenesis and/or hyaluronic acid genesis and/or elastinogenesis upon irradiation by visible light in a wavelength range of 570 to 780 nm and/or upon irradiation by non-visible light in a wavelength range of from 810 nm to 850 nm, wherein the method comprises irradiating at least a part of the skin by using the device of claim 1.

\* \* \* \* \*